(12) United States Patent
Falk

(45) Date of Patent: Apr. 24, 2012
(10) Patent No.: US 8,162,956 B2

(54) DEVICE FOR FOOTCARE

(75) Inventor: Henrik Falk, Stockholm (SE)

(73) Assignee: Falk Inventions AB, Stockholm (SE)

( * ) Notice: Subject to any disclaimer, the term of this patent is extended or adjusted under 35 U.S.C. 154(b) by 33 days.

(21) Appl. No.: 11/913,755

(22) PCT Filed: May 9, 2006

(86) PCT No.: PCT/SE2006/000549
§ 371 (c)(1),
(2), (4) Date: Dec. 12, 2007

(87) PCT Pub. No.: WO2006/121392
PCT Pub. Date: Nov. 16, 2006

(65) Prior Publication Data
US 2008/0195117 A1    Aug. 14, 2008

(30) Foreign Application Priority Data
May 10, 2005 (SE) ...................................... 0501046

(51) Int. Cl.
*A45D 29/18* (2006.01)
(52) U.S. Cl. ...................................... 606/131; 132/76.4
(58) Field of Classification Search .................... 30/169; 132/76.4–76.5; 606/131, 167; 4/571.1, 574.1, 4/583, 606, 622; 451/490, 494, 495, 523, 451/524, 552, 557, 913; 601/27–29
See application file for complete search history.

(56) References Cited

U.S. PATENT DOCUMENTS

| | | | | |
|---|---|---|---|---|
| 953,171 A * | 3/1910 | Kraeuter | .......................... | 30/169 |
| 1,955,848 A * | 4/1934 | Dunn | .............................. | 76/81.8 |
| 4,206,574 A * | 6/1980 | Dotsko | .......................... | 451/495 |
| 5,228,151 A * | 7/1993 | Livingston-Capoano | ..... | 4/574.1 |
| 6,142,156 A | 11/2000 | Brunderman | | |
| 2002/0088471 A1* | 7/2002 | Sullinger | ..................... | 132/76.4 |
| 2006/0196520 A1* | 9/2006 | Anderson et al. | ............ | 132/76.4 |

FOREIGN PATENT DOCUMENTS

SE        512 447 C2    3/2000

* cited by examiner

*Primary Examiner* — S. Thomas Hughes
*Assistant Examiner* — Ashley Cronin
(74) *Attorney, Agent, or Firm* — Dickstein Shapiro LLP

(57) ABSTRACT

The present invention relates to an apparatus for footcare, which comprises an abrasive body (1) and members for supporting the abrasive body (1) relatively a ground, the abrasive body (1) has an external surface, and the external surface is at least partly abrasive, whereby the portion of the external surface of the abrasive body (1) that is abrasive comprises a number of partial surfaces, and these partial surfaces comprises at least a concave surface (9, 12) and a convex surface (10, 15). A main surface (9), which at the position of the abrasive body (1) on the ground is faced upwardly, has two concave partial surfaces (A, B) angled against each other, whereby a first part-surface (A) has an angle in the range 15-45° in relation to the ground and a second partial surface (B) has an angle up to 15° in relation to the ground.

18 Claims, 3 Drawing Sheets

DEVICE FOR FOOTCARE

TECHNICAL AREA OF THE INVENTION

The present invention relates to an apparatus for footcare, which comprises an abrasive body and members for supporting the abrasive body relatively a ground, that the abrasive body presents an external surface, and that the external surface is at least partly abrasive.

STATE OF THE ART

By SE-C-512 447 is previously known an apparatus for footcare, whereby this apparatus comprises a flat-shaped basic part, whereby an abrasive material is applied on at least one side of this basic part. The abrasive material is preferably made of an abrasive cloth. In the case the flat-shaped basic part is provided with abrasive cloths on both of its sides, these will preferably be of different degree of coarseness. The apparatus is primarily intended to be used by many persons, with a handicap and/or limited ability to move, whereby the flat-shaped basic part for this purpose is provided with bulges of frictional material at two opposite edges. In that way, the apparatus can be placed inclined between a wall and a floor without any risk that it may slide.

Another known apparatus for footcare is U.S. Pat. No. 5,913,313.

THE OBJECTS AND THE FEATURES OF THE INVENTION

A primarily object with the present invention is to present an apparatus of the defined kind mentioned above, which offers the user different alternatives for adaptation to the part of the foot that shall be taken care of.

An additional object with the present invention is that it shall not involve the hands of the user.

Yet an object with the present invention is that it is extraordinarily compact in its shape.

At least the primarily object with the present invention is realisable by means of an apparatus according to the defined kind mentioned above, that has obtained the denoted features in the following independent claim.

Preferred embodiments are defined in the dependent claims.

SHORT DESCRIPTION OF THE DRAWINGS

Hereinafter, a preferred embodiment of the invention will be described by reference to the attached drawings, in which.

DETAILED DESCRIPTION OF PREFERRED EMBODIMENTS OF THE INVENTION

Figure 1:
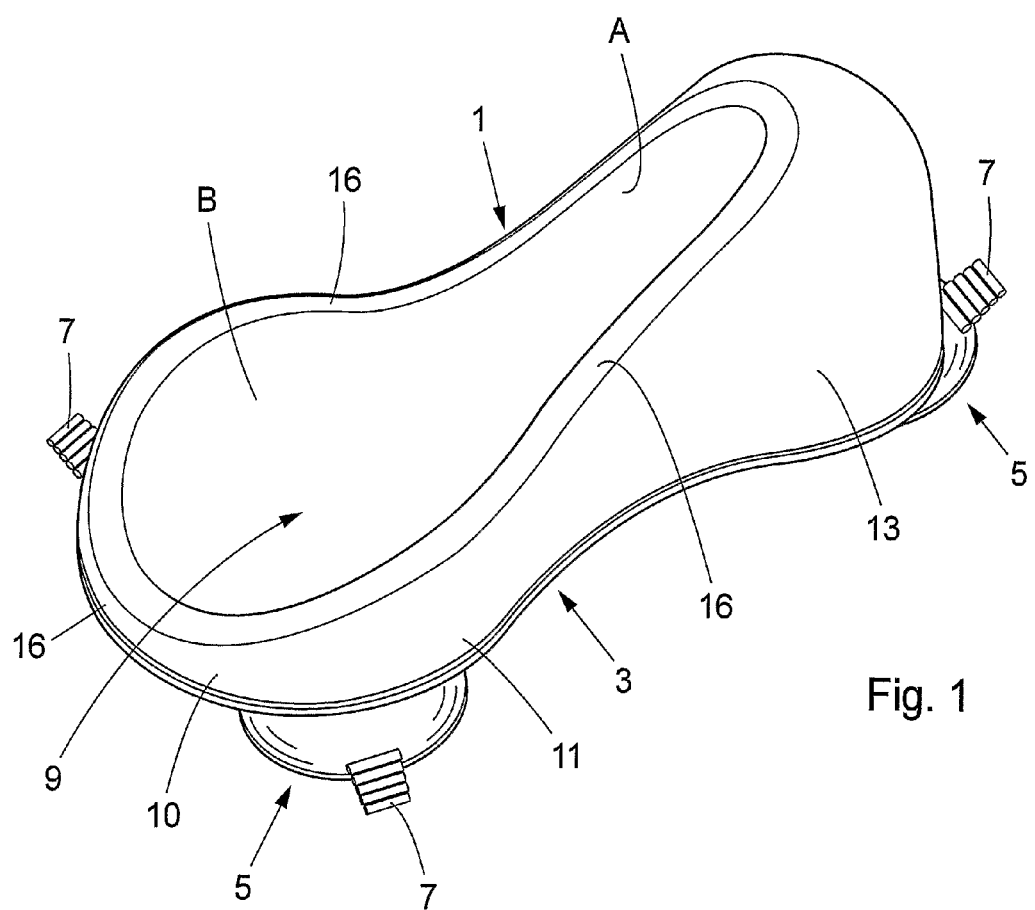
FIG. 1 shows a perspective view, seen obliquely from above, of an apparatus according to the present invention.
Figure 2:
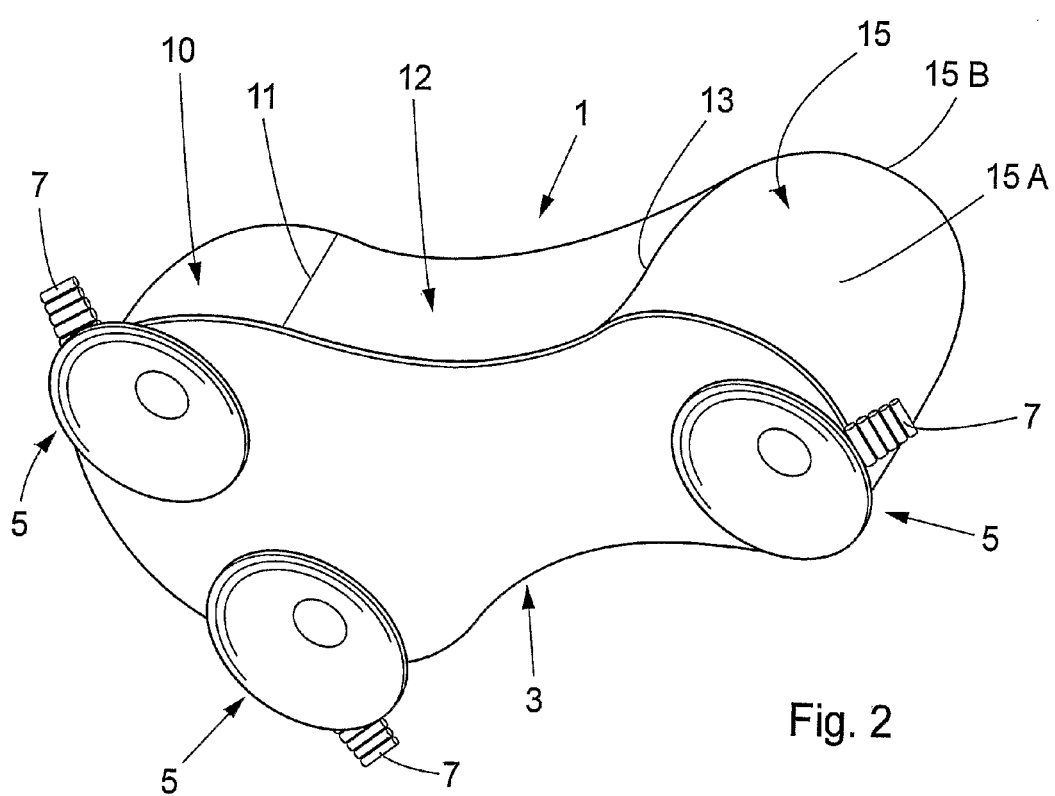
FIG. 2 shows a perspective view, seen obliquely from below, of the apparatus according to FIG. 1.

The shown apparatus for footcare in FIGS. 1 and 2 comprises an abrasive body 1 and a base plate 3, whereby the abrasive body 1 and the base plate 3 are connected to each other in a suitable way, for example by gluing. The abrasive body 1 is preferably in the shape of a shell, whereby the open end that is defined by the shell has a shape that corresponds to the shape that is defined by the circumference of the base plate 3. In another variation, the abrasive body 1 is a solid body or at least a partly solid body.

The base plate 3 is plane in the shown embodiment and provided with three suction cups 5, which are permanently connected with the base plate 3. Of course the number of suction cups can be more or fewer. Two suction cups 5 are arranged in the area of one end of the apparatus while one suction cup 5 is arranged in the area of the other end of the apparatus. Each of the suction cups 5 are provided with a tab 7, which is connected to a suction cup 5 in the vicinity of the periphery of the suction cup 5. The tabs 7 are used when the suction cups 5 should be loosen from a ground. By pulling a tab 7, air will enter under the suction cup 5 and it will come loose from the ground. The advantage by having three suction cups 5 is that necessary stability is obtained, at the same time as the abrasive body 1 easily can be loosen from the ground. In order to loosen the abrasive body 1 from the ground, one pulls with each hand in the two suction cups 5 that are arranged in the one end of the abrasive body 1. Then, one hand remains under the end of the abrasive body 1 as a distance, such that the suction cups not will adhere to the ground again. Simultaneously, one loosens the last suction cup 5 with the other hand.

In general, the shape of the apparatus according to the invention associate with a foot, whereby the apparatus in general has different height in the area of its two ends. If the reference to a foot is kept, the apparatus has a greater height in the area of the heel and a shorter height in the area of the toes. The area for the heel forms the rear part while the area of the toes forms the front part of the apparatus.

The abrasive body 1 is made up of a number of bulging surfaces, where these bulging surfaces are both convex and concave. According to a preferred embodiment, the whole external surface of the abrasive body 1 is abrasive, i.e. it has a structure such that a rubbing occurs of the actual part of the foot, when a part of the foot slides against the abrasive body 1. The rubbing effect that is exerted by the abrasive surface varies, depending on the structure of the abrasive surface. From a general point of view, a coarser structure results in a larger rubbing effect. Within the scope of the invention, it is conceivable that the abrasive body 1 has varying abrasive structure at different parts of the abrasive body 1.

The abrasive body 1 comprises a main surface 9, which generally is concave/cup-shaped and divided in two partial surfaces, one first partial surface A and a second partial surface B, respectively. Seen in a plane view of the apparatus according to the present invention, the main surface 9 has a pear-shape. Due to the general shape of the apparatus according to the present invention, the more narrow part of the main surface 9, i.e. the partial surface A, is located on a higher level than the wider part of the main surface 9, i.e. the partial surface B.

Figure 3:
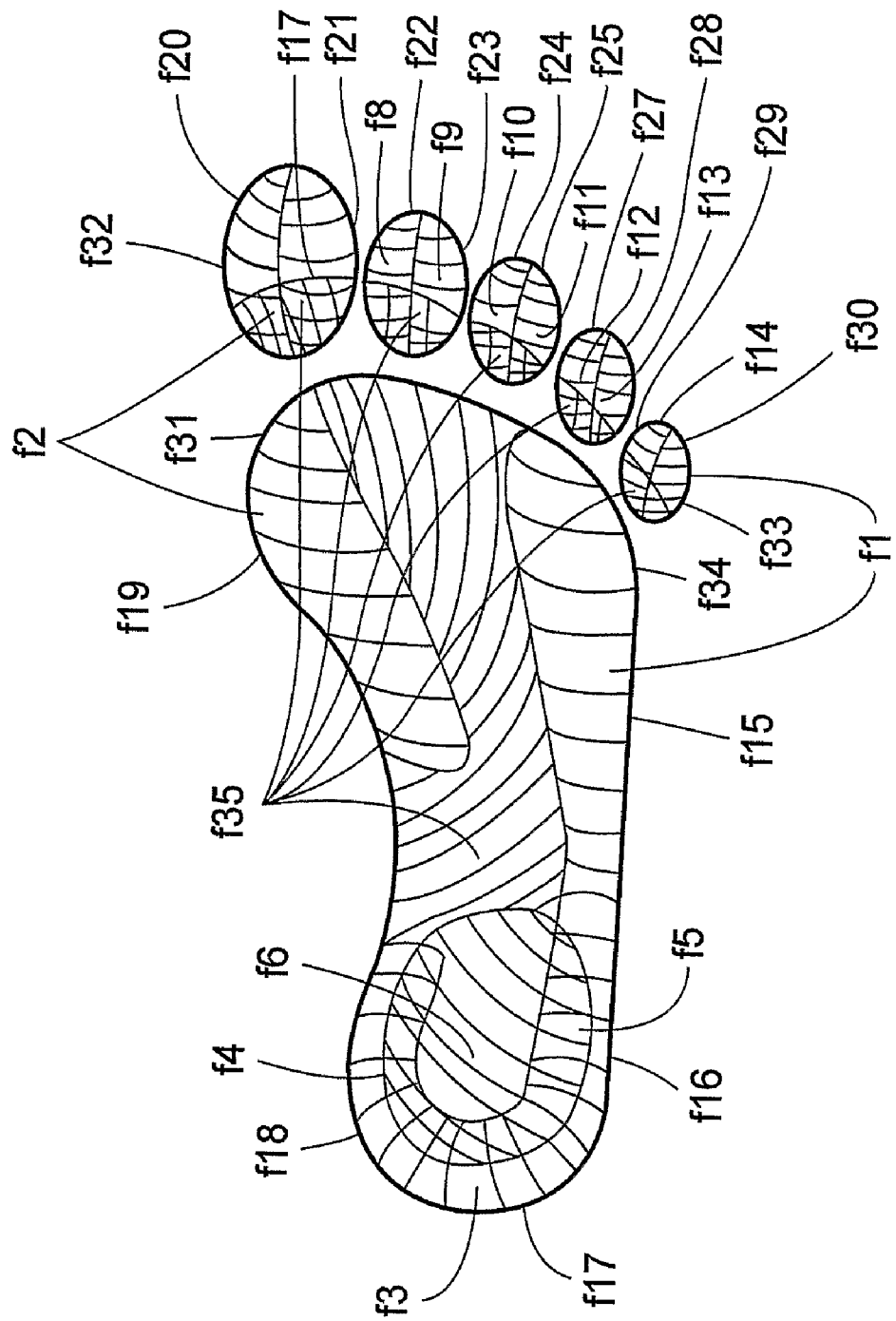
FIG. 3 shows a foot from below having different areas that may need to be treated.

The partial surfaces A and B are each located in separate angles against the horizontal plane when the abrasive body 1 is placed on a horizontal ground. Thus, the two surfaces A and B have a mutual angular relationship. In order to reach a satisfactory effect, the partial surface A presents an angle of 15-45° against the horizontal plane, preferably 25-35° and most preferred 30° for the best effect. The advantage with this inclination is that the partial surface A may bring the pressure of the foot forward over the abrasive surface and a maximal rubbing ability is obtained by a natural motion. Accordingly, callosities and the like at the side areas of the foot f1-f5, see FIG. 3, are removed. As a suggestion, the partial surface A can be concave with a concaveness diameter of 10 cm.

The partial surface B has instead an angle up to 15° against the horizontal plane, preferably up to 10° and more preferred up to 5°. This partial surface B is preferably open and cup-shaped with e.g. a concaveness diameter of 16 cm. Preferably, the partial surface B has a diameter of about 10 cm. The cup-shaped partial surface B is for exfoliation of the areas f3-f6 of the heel, see FIG. 3, which is done by a natural rotary motion. Accordingly, the abrasive body 1 is provided with an inclined slope, i.e. the partial surface A, that passes over to an opened cup-shape, i.e. the partial surface B. By the motion of the foot over the inclined slope A down into the opened cup-shape, an improved grinding effect is created equally over the front portion of the sole of the foot f2, f19, f31 and f32 and f1, f15 and f33, see FIG. 3.

The abrasive body 1 comprises also a substantially circular cylindrical surface 10 in the area of its front part, whereby this circular cylindrical surface generally has a vertically extension when the apparatus according to the present invention is placed on a horizontal ground. The circular cylindrical surface 10 is not confined, but extends only along a portion of a circumference of a cylinder. The extension of the circular cylindrical surface 10 in the direction of the circumference has been indicated with two first boundary lines 11 (only one of them is evident in FIGS. 1 and 2), which first boundary lines 11 extends substantially perpendicular against the base plate 3.

When the user puts the outer ends of the toes against the vertical, circular cylindrical surface 10, and by a rotary motion around the heel, the toes front sides are removed by file f20-30, see FIG. 3. Also the toenails are filed off as an additional effect.

The abrasive body 1 comprises also two substantially concave, second side surfaces 12, which are located in an intermediary portion of the apparatus according to the present invention. Down in the lower part, the side surfaces 12 connects against the base plate 3, and at the top against the main surface 5. Each of the secondary side surfaces 12 starts from the first boundary line 11 and extends sideways to a second boundary line 13, which likewise extends substantially perpendicular against the base plate 3. Due to the general shape of the apparatus, the second side surfaces 12 have a greater height at its connection to the second boundary lines 13 than at its connection to the first boundary lines 11.

When the user goes up and down on tiptoe, a natural vertical motion is achieved, such that abrasion can occur on the vertical sides f16-18 of the heel. Also the front sides f15, f19 of the sole of the foot, in the area where the thicker skin of the sole of the foot passes over to skin of normal kind, can be exactly removed on these two sides 12 through broad control of the pressure against the vertical, abrasive side 12 by the user. In addition, the front ends of the toes, f20-f30, and the toenails can be filed off. Preferably, the concave surface 12 has a diameter of about 16 cm.

The abrasive body 1 comprises also a convex, third side surface 15, which is located in the area of the rear end of the apparatus. The third side surface 15 comprises a circular cylindrical portion 15A, whereby this circular cylindrical portion 15A not forms a confined cylinder but extends between the two second boundary lines 13 and connects against the base plate 3. The circular cylindrical portion 15A is preferably somewhat sloping against the vertical plane, up to 20°. By tilting the heel against the floor and raising and lowering the front part of the foot, an abrasion can occur at f31-34, see FIG. 3.

The exfoliation occurs, due to the sloping, at the desired portion at the passage between thick and thin skin. These vertical surfaces provides vertical abrasive surfaces, which results in improved abrasion for the inside and the interfaces towards the upper parts of the sole of the foot where the skin is more delicate. In that case, the user has more control of the exfoliation, owing to that the user can control the bearing pressure against the vertical surface.

The third side surface 15 comprises also a dome-shaped portion 15B, which defines the upper located part of the convex, third surface 15 when the apparatus according to the present invention is placed on a horizontal ground. By a natural motion, the user exfoliates thick skin in the area of the arch, the middle of the sole of the foot and the rear part of the toes f35, see FIG. 3.

At all the boundary lines 11 and 13 of the apparatus according to the present invention, a passage occurs between the shape of the connecting surfaces of the boundary lines 11, 13, i.e. from concave to convex or vice versa. Above it has been described that the first and second side surfaces 10, 12 are substantially vertical, while the third side surface is inclined up to 20° against the vertical plane. Another distribution can be possible of course, where at least one side surface is substantially vertical and one side surface has an inclination up to 20° against the vertical plane.

The passage between the main surface 9 and the connecting surfaces is done through a gently rounded, convex portion 16 that mainly extends around the whole main surface 9. Preferably, the rounding has a radius of about 5 mm, whereby a gently rounded, somewhat elevated edge C is formed. This edge C is suitable for exfoliation between the toes, f7-14, and provides simultaneously support for the toes when these are passed along the edge C. Through the inclination and the ergonomically toe-adapted rounding of the edge C, the toes are separated in a natural way at pressure against the abrasive body 1. At the lower part of the edge C, an additional excellent effect on the specifically demanding portion f21 of the big toe is obtained.

Preferably the abrasive body is symmetrical in longitudinal direction. Accordingly, the abrasive body 1 can be used for both right and left foot without needing to turn it around.

POSSIBLE MODIFICATION OF THE INVENTION

In the above described embodiment, the whole external surface of the abrasive body is formed as an abrasive surface. However, within the scope of the present invention, it is still possible that only portions of the external surface of the abrasive body are abrasive.

In the above described embodiment, the apparatus comprises a shell-shaped abrasive body and a base plate connected to the abrasive body. Within the scope of the present invention, it is still conceivable that the abrasive body is made of a solid body with a plane surface, facing the ground that supports the apparatus according to the present invention. It is also possible, if the abrasive body is shell-shaped, that it is provided with members for supporting the shell-shaped abrasive body relatively a ground.

The above described apparatus according to the present invention has a shape that associate with a foot. Within the scope of the present invention, it is not required that the apparatus presents this shape. However, a basic principle of the present invention is that the apparatus according to the invention shall comprise both concave and convex abrasive surfaces.

The invention claimed is:
1. Apparatus for footcare, which comprises:
   an abrasive body and members for supporting the abrasive body relative to a ground, the abrasive body having a longitudinal axis and an external surface, at least a portion of the external surface being at least partly abrasive, wherein a main surface of the abrasive body, which at the position of the abrasive body on the ground is faced upwardly, has two concave surfaces angled against each other along an orthogonal axis that is orthogonal to the longitudinal axis of the abrasive body, whereby a first concave surface has an angle along the longitudinal axis in the range of 15-45° in relation to the ground and a second concave surface has an angle along the longitudinal axis of less than 15° in relation to the ground, and wherein the abrasive body further comprises an abrasive edge substantially surrounding the entire main surface, said abrasive edge comprising a rounded convex surface.

2. Apparatus according to claim 1, wherein the second concave surface is cup-shaped.

3. Apparatus according to claim 2, wherein the first concave surface and the cup-shaped second concave surface provide an inclined slope passing over to an opened-cup shape.

4. Apparatus according to claim 3, wherein said main surface is configured to receive a foot such that said inclined slope passing over to an opened-cup shape provides a grinding effect equally over a front portion of a sole of a foot.

5. Apparatus according to claim 1, further comprising an abrasive, convex, first side surface connected to the abrasive edge.

6. Apparatus according to claim 5, further comprising an abrasive, concave, second side surface connected to the abrasive edge.

7. Apparatus according to claim 6, further comprising an additional abrasive, convex, third side surface connected to the abrasive edge.

8. Apparatus according to claim 7, wherein at least one of the first, second and third side surfaces is vertical against the main surface.

9. Apparatus according to claim 7, wherein at least one of the first, second and third side surfaces has an inclination up to 20° against the vertical plane.

10. Apparatus according to claim 7, wherein the convex, third side surface comprises a dome-shaped portion.

11. Apparatus according to claim 1, wherein the members for supporting the abrasive body comprise suction cups.

12. Apparatus according to claim 11, wherein the number of suction cups is three.

13. Apparatus according to claim 1, wherein the abrasive body further comprises:

a front part and a rear part at opposite ends of the longitudinal axis of the abrasive body; and a first side and a second side on opposite sides of the longitudinal axis of the abrasive body, wherein the first concave surface is located on one of the front and the rear parts, and the second concave surface is located on the other of the front and the rear parts.

14. Apparatus according to claim 13, wherein the first concave surface is located on a higher level than the second concave surface.

15. Apparatus according to claim 13, wherein the front part has a front width along the orthogonal axis and the rear part has a rear width along the orthogonal axis, said apparatus further comprising a middle part located longitudinally between the front part and the rear part, wherein the middle part has a width along the orthogonal axis that is less than the front and rear widths.

16. Apparatus according to claim 15, wherein the front width is greater than the rear width.

17. Apparatus according to claim 1, wherein the rounded convex surface of the abrasive edge has a radius of approximately five millimeters.

18. Apparatus according to claim 1, wherein the first concave surface and the second concave surface have different concaveness diameters.

* * * * *